(12) United States Patent
Buddemeyer et al.

(10) Patent No.: US 9,987,107 B2
(45) Date of Patent: Jun. 5, 2018

(54) MANDIBULAR REPOSITIONING DEVICE

(71) Applicants: Darren Buddemeyer, Frontenac, MO (US); John J. Pietroborgo, Belleville, IL (US); Matthew K. Malabey, Wentzville, MO (US)

(72) Inventors: Darren Buddemeyer, Frontenac, MO (US); John J. Pietroborgo, Belleville, IL (US); Matthew K. Malabey, Wentzville, MO (US)

(73) Assignee: Ortho Solutions, LC, St. Ann, MO (US)

(*) Notice: Subject to any disclaimer, the term of this patent is extended or adjusted under 35 U.S.C. 154(b) by 0 days. days.

(21) Appl. No.: 14/756,681

(22) Filed: Sep. 29, 2015

(65) Prior Publication Data

US 2016/0100915 A1    Apr. 14, 2016

Related U.S. Application Data

(60) Provisional application No. 62/122,101, filed on Oct. 10, 2014.

(51) Int. Cl.
*A61C 7/36* (2006.01)
*A61C 7/18* (2006.01)
*A61C 7/28* (2006.01)

(52) U.S. Cl.
CPC .............. *A61C 7/36* (2013.01); *A61C 7/18* (2013.01); *A61C 7/282* (2013.01)

(58) Field of Classification Search
CPC .............. A61C 7/18; A61C 7/36; A61C 7/282
USPC .................................. 128/861; 433/6, 19, 24
See application file for complete search history.

(56) References Cited

U.S. PATENT DOCUMENTS

| | | | | |
|---|---|---|---|---|
| 4,525,143 A | * | 6/1985 | Adams | A61C 7/12 433/5 |
| 4,551,095 A | * | 11/1985 | Mason | A61C 7/36 433/19 |
| 5,324,196 A | | 6/1994 | Magill | |
| 5,443,384 A | * | 8/1995 | Franseen | A61C 7/36 433/18 |

(Continued)

FOREIGN PATENT DOCUMENTS

DE    10042049 A1 * 3/2002 ............... A61C 7/00

*Primary Examiner* — Yogesh Patel
*Assistant Examiner* — Drew Folgmann
(74) *Attorney, Agent, or Firm* — Paul M. Denk

(57) ABSTRACT

A mandibular repositioning device having a lower assembly having a buccal tube having a slot opening formed therein with the tube being connected to a molar bracket that fits over a molar, a lower wedge having a head portion having an inner contact surface, and an integral extension portion with the extension portion being adapted for insertion into the slot opening for adjustment purposes, and an upper assembly having a buccal tube having a slot opening formed therein with the tube being connected to a molar bracket that fits over a molar, an upper wedge having a head portion having an outer rounded contact surface, and an integral extension portion, the extension portion being adapted for insertion into the slot opening for adjustment purposes. Set screws are adapted for contacting the extension portions for holding the upper wedge and lower wedge in place with the outer rounded contact surface bearing against the inner contact flat surface for repositioning a mandibular jaw.

1 Claim, 3 Drawing Sheets

(56) References Cited

U.S. PATENT DOCUMENTS

| | | | |
|---|---|---|---|
| 5,645,424 A * | 7/1997 | Collins, Jr. | A61C 7/36 433/18 |
| 5,678,990 A | 10/1997 | Rosenberg | |
| 5,848,891 A * | 12/1998 | Eckhart | A61C 7/36 433/19 |
| 5,967,774 A * | 10/1999 | Teramoto | A61C 7/282 433/18 |
| 6,491,519 B1 * | 12/2002 | Clark | A61C 7/00 433/18 |
| 2004/0131989 A1 * | 7/2004 | Dellinger | A61C 7/00 433/18 |
| 2004/0197724 A1 * | 10/2004 | Wilkerson | A61C 7/282 433/17 |
| 2005/0028826 A1 * | 2/2005 | Palmisano | A61F 5/566 128/848 |

* cited by examiner

MANDIBULAR REPOSITIONING DEVICE

CROSS REFERENCE TO RELATED APPLICATION

This non-provisional patent application claims priority to the provisional patent application having Ser. No. 62/122,101, filed on Oct. 10, 2014.

FIELD OF THE DISCLOSURE

This disclosure generally relates to orthodontic devices for assisting in orthodontic treatments or procedures, and more particularly to a mandibular repositioning device for repositioning the lower jaw relative to the upper jaw in order to improve occlusion.

BACKGROUND

Orthodontists treat patients by controlling the movement and displacement of teeth or the jaws in a mouth by use of various orthodontic devices and procedures. Movement or rotation of a tooth within the mouth may be accomplished through the use of external forces applied to the tooth. To ensure that the moved or treated tooth remains in a desired location in the jaw bone, an external force is applied to the tooth for an extended period of time. Once the tooth has reached a desired position or orientation, the force may be removed. Some examples of devices used to apply the necessary force to the tooth are brackets, buccal tubes, wires, clamps, or rubber bands.

Another known orthodontic condition that needs treatment concerns the correction of the alignment of the lower jaw relative to the upper jaw. For example, a patient may have a malocclusion condition where the lower jaw is positioned an excessive distance in a rearward direction from the upper jaw when both of the jaws are closed. This condition is commonly known as an overbite. Another malocclusion condition is one where the lower jaw of a patient protrudes up and outward abnormally partially overlapping upper teeth or jaw when both of the jaws are closed. This condition is commonly known as an underbite. Unlike an overbite which is extremely common, underbites only affect 5-10% of the world's population. In order to treat these malocclusion conditions, orthodontists have invented various apparatuses.

Various devices have been proposed and used to attempt to correct the malocclusion conditions of overbite and underbite. For example, a force-applying device such as a headgear device that includes strapping that extends around the head of the patient and connects to various brackets attached to the teeth has been used. Since headgear is worn outside the mouth, it has been found unacceptable to some patients due to the embarrassment of wearing it. Some intra-oral devices have been developed and used to attempt to correct malocclusion conditions. Such devices include telescoping mechanisms, pins, rods, elastic materials, chains, or the Herbst appliance. These devices can be bulky, impede tongue mobility, are uncomfortable to wear, and interfere with good oral hygiene.

The present disclosure is designed to obviate and overcome many of the disadvantages and shortcomings experienced with prior orthodontic devices. Moreover, the present disclosure is related to a mandibular repositioning device that can reposition the lower jaw relative to the upper jaw to correct a malocclusive condition. Further, it would be advantageous to have a mandibular repositioning device that can be easily adjusted, or incrementally adjusted, to correct a malocclusion condition.

SUMMARY

The present disclosure is a mandibular repositioning device which comprises a lower assembly having a buccal tube having a slot opening formed therein with the tube being connected to a molar bracket or crown like member, that fits over a molar, a lower wedge having a head portion having an inner contact surface, an outer rounded surface, and an extension portion with the extension portion being adapted for insertion into the slot opening for adjustment purposes, the tube further having a side opening through which is inserted a set screw that is adapted for contacting the extension portion for holding the lower wedge in place, and an upper assembly having a buccal tube having a slot opening formed therein with the tube being connected to a molar bracket that fits over a molar, an upper wedge having a head portion having an outer rounded contact surface, an inner surface, and an extension portion, the extension portion being adapted for insertion into the slot opening for adjustment purposes, the tube further having a side opening through which is inserted a set screw that is adapted for contacting the extension portion for holding the upper wedge in place with the outer rounded contact surface bearing against the inner contact surface for repositioning a mandibular jaw.

In another form of the present disclosure, a mandibular repositioning device comprises a pair of lower assemblies each having a buccal tube having a slot opening formed therein with the tube being connected to a molar bracket that fits over a molar, a lower wedge having a head portion having an inner contact surface, an outer rounded surface, and an extension portion with the extension portion being adapted for insertion into the slot opening for adjustment purposes, the tube further having a side opening through which is inserted a set screw that is adapted for contacting the extension portion for holding the lower wedge in place, and a pair of upper assemblies each having a buccal tube having a slot opening formed therein with the tube being connected to a molar bracket that fits over a molar, an upper wedge having a head portion having an outer rounded contact surface, an inner surface, and an extension portion, the extension portion being adapted for insertion into the slot opening for adjustment purposes, the tube further having a side opening through which is inserted a set screw that is adapted for contacting the extension portion for holding the upper wedge in place with each of the outer rounded contact surfaces bearing against each of the inner contact surfaces for repositioning a mandibular jaw.

In yet another form of the present disclosure, a mandibular repositioning device is disclosed which comprises a left lower assembly having a buccal tube having a slot opening formed therein with the tube being connected to a molar bracket that fits over a molar, a lower wedge having a head portion having an inner contact surface, an outer rounded surface, and an extension portion with the extension portion being adapted for insertion into the slot opening for adjustment purposes, the tube further having a side opening through which is inserted a set screw that is adapted for contacting the extension portion for holding the lower wedge in place, a right lower assembly having a buccal tube having a slot opening formed therein with the tube being connected to a molar bracket that fits over a molar, a lower wedge having a head portion having an inner contact surface, an outer rounded surface, and an extension portion with the extension portion being adapted for insertion into the slot opening for adjustment purposes, the tube further having a side opening through which is inserted a set screw that is adapted for contacting the extension portion for holding the lower wedge in place, a left upper assembly having a buccal tube having a slot opening formed therein with the tube being connected to a molar bracket that fits over a molar, an upper wedge having a head portion having an outer rounded contact surface, an inner surface, and an extension portion, the extension portion being adapted for insertion into the slot opening for adjustment purposes, the tube further having a side opening through which is inserted a set screw that is adapted for contacting the extension portion for holding the upper wedge in place with the outer rounded contact surface bearing against the inner contact surface for repositioning a mandibular jaw, and a right upper assembly having a buccal tube having a slot opening formed therein with the tube being connected to a molar bracket that fits over a molar, an upper wedge having a head portion having an outer rounded contact surface, an inner surface, and an extension portion, the extension portion being adapted for insertion into the slot opening for adjustment purposes, the tube further having a side opening through which is inserted a set screw that is adapted for contacting the extension portion for holding the upper wedge in place with the outer rounded contact surface bearing against the inner contact surface for repositioning a mandibular jaw.

In light of the foregoing comments, it will be recognized that the present disclosure provides a mandibular repositioning device for use in orthodontic procedures to correct a malocclusion condition of the jaws.

The present disclosure provides a mandibular repositioning device that can be easily employed with highly reliable results to be placed onto the lower jaw and the upper jaw to exert a force on the lower jaw to reposition the lower jaw relative to the upper jaw.

The present disclosure also provides a mandibular repositioning device that may be used to align the lower jaw relative to the upper jaw in incremental treatments.

The present disclosure further provides a mandibular repositioning device that may be temporarily placed on teeth to reposition the lower jaw relative to the upper jaw.

The present disclosure provides a mandibular repositioning device that requires only a few tools for inserting or removing the device from the teeth.

The present disclosure provides a mandibular repositioning device that can reposition the lower jaw in a forward direction relative to the upper jaw to correct an overbite condition.

The present disclosure is also directed to a mandibular repositioning device that can reposition or move the lower jaw in a backward direction relative to the upper jaw to correct an underbite condition.

The present disclosure provides a mandibular repositioning device that is placed inside the mouth, is not bulky, and has few moving parts.

These and other advantages of the present disclosure will become apparent to those skilled in the art after considering the following detailed specification in conjunction with the accompanying drawings.

DETAILED DESCRIPTION OF PREFERRED EMBODIMENTS

Figure 1:
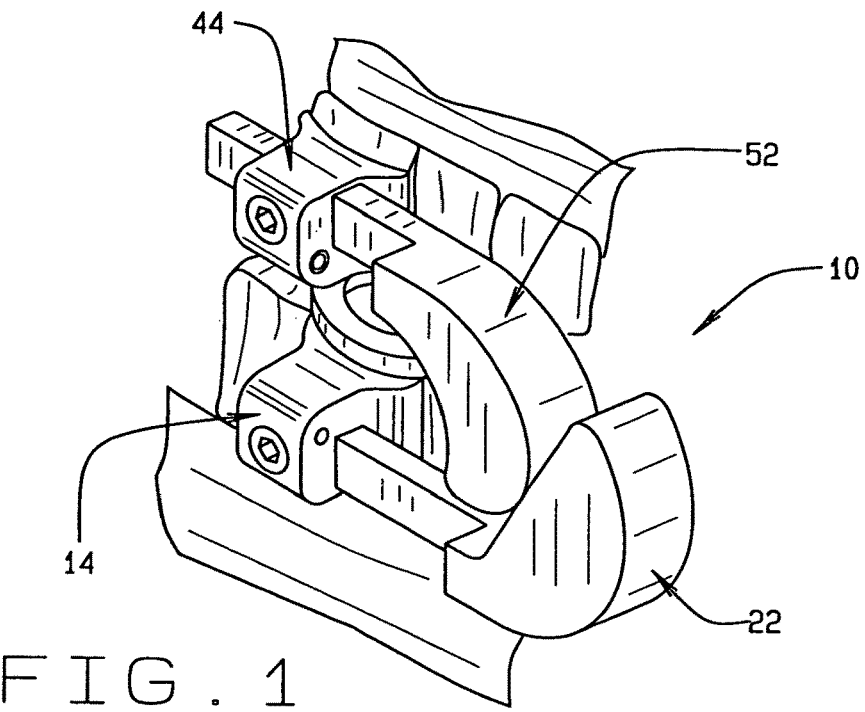
FIG. 1 is a side perspective view of a mandibular repositioning device constructed according to the present disclosure, shown being positioned on a right side of a mouth of a patient.
Figure 2:
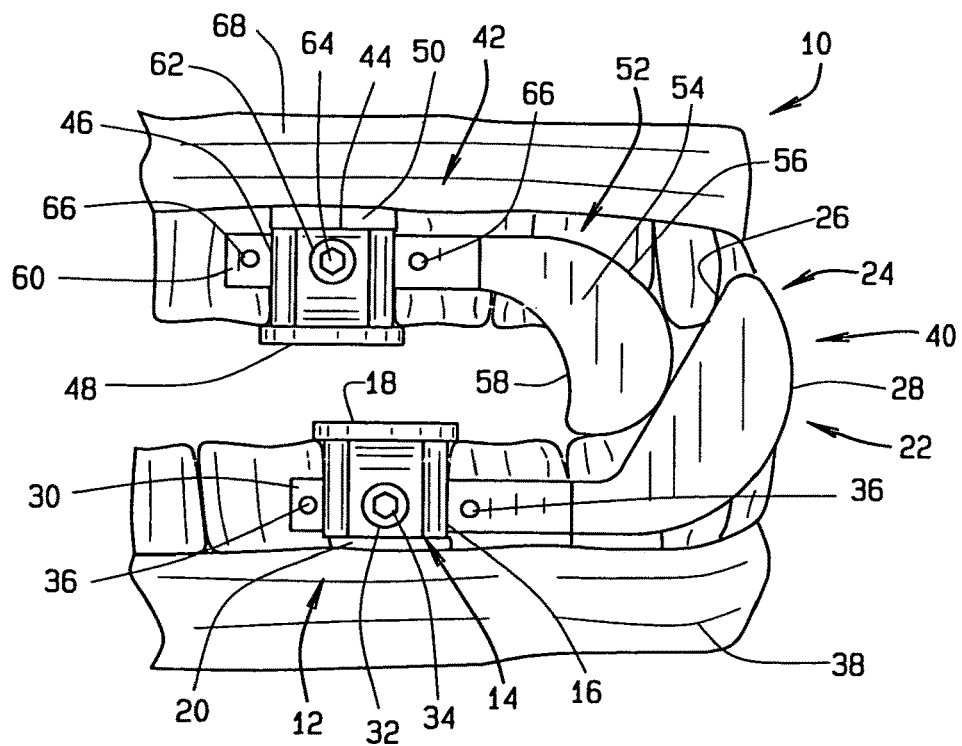
FIG. 2 is a perspective view of a lower right buccal tube constructed according to the present disclosure.

Referring now to the drawings, wherein like numbers refer to like items, number 10 identifies a preferred embodiment of a mandibular repositioning device constructed according to the present disclosure. With reference now to FIG. 1, the mandibular repositioning device 10 comprises a lower assembly 12 having a buccal tube 14 having a slot opening 16 formed therein with the tube 14 being welded or connected to a molar bracket 18 that fits around or over a molar 20. See also FIG. 2. A lower wedge 22 has a head portion 24 having an inner contact surface 26, an outer rounded surface 28, and an extension portion 30. The extension portion 30 is adapted for insertion into the slot opening 16 for adjustment purposes. The tube 14 also has a side opening 32 through which is inserted a hex head set screw 34 that is adapted for contacting the extension portion 30 for holding the lower wedge 22 in place. The extension portion 30 may have various indentations 36 for receiving or fixing the hex head set screw 34 at various positions. The lower assembly 12 is shown being placed over the molar 20 of a lower or mandibular jaw 38 of a right side of a mouth 40.

The mandibular repositioning device 10 further comprises an upper assembly 42 having a buccal tube 44 having a slot opening 46 formed therein with the tube 44 being welded or connected to a molar bracket 48 that fits around or over a molar 50. An upper wedge 52 has a head portion 54 having an outer rounded contact surface 56, an inner surface 58, and an extension portion 60. The extension portion 60 is adapted for insertion into the slot opening 46 for adjustment purposes. The tube 44 also has a side opening 62 through which is inserted a hex head set screw 64 that is adapted for contacting the extension portion 60 for holding the upper wedge 52 in place. The extension portion 60 may have various indentations 66 for receiving or fixing the hex head set screw 64 at various positions. The upper assembly 42 is shown being placed over the molar 50 of an upper or maxillary jaw 68 of the mouth 40. The outer rounded contact surface 56 is used to bear against the inner contact surface 26 to reposition the lower jaw 38 relative to the upper jaw 68. As can be appreciated, the wedges 22 and 52 can be adjusted when necessary until a proper repositioning or alignment of the lower jaw 38 relative to the upper jaw 68 is accomplished. Although not shown in this particular view, as will be pointed out herein, there may be a left lower assembly and a left upper assembly on the left side of the mouth 40.

Figure 3:
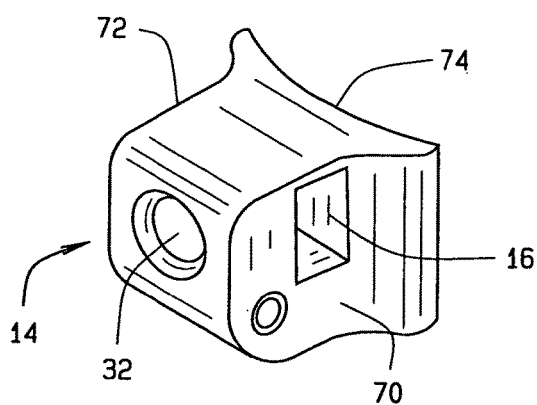
FIG. 3 is a perspective view of an upper right buccal tube constructed according to the present disclosure.

FIG. 3 is a perspective view of the lower right buccal tube 14. The tube 14 has the opening 16 formed therein and the side opening 32. The side opening may be threaded. The tube 14 has a front side 70 and a back side 72. The side opening 32 is in an offset position on the front side 70. The tube 14 also has a curved attachment side 74. The side 74 is used for welding or connecting the tube 14 to the bracket 18.

Figure 4:
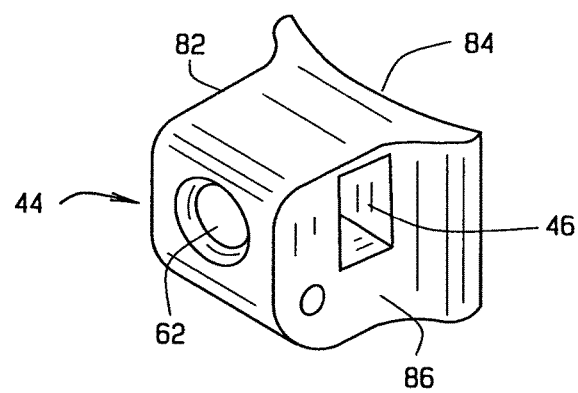
FIG. 4 is a perspective view of a lower right wedge constructed according to the present disclosure.

Referring now to FIG. 4, a perspective view of the upper right buccal tube 44 is shown. The upper right buccal tube 44 has the opening 46 formed therein and the side opening 62 that is used to receive the set screw 64. The tube 44 has a front side 80 and a back side 82. The side opening 62 is in an offset position on the front side 80. The tube 44 also has a curved attachment side 84. The side 84 is used for welding or connecting the tube 44 to the molar bracket 48.

Figure 5:
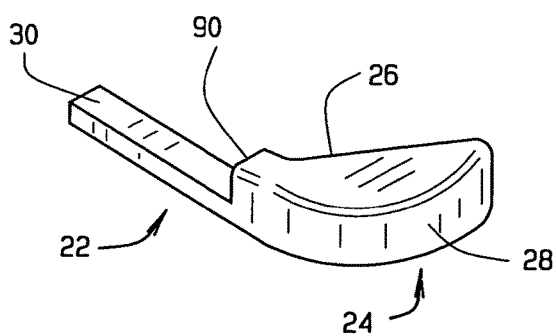
FIG. 5 is a perspective view of an upper right wedge constructed according to the present disclosure.

FIG. 5 illustrates a perspective view of the lower wedge 22. The lower wedge 22 has the head portion 24 having the inner contact surface 26, the outer rounded surface 28, and the extension portion 30. The extension portion 30 is adapted for insertion into the slot opening 16 of the tube 14 for adjustment purposes. The head portion 24 also has a stop portion or surface 90 that is capable of contacting the front side 70 of the tube 14. Although not shown in this particular view, the lower wedge 22 may have indentations 36 formed in the extension portion 30, as has been explained.

Figure 6:
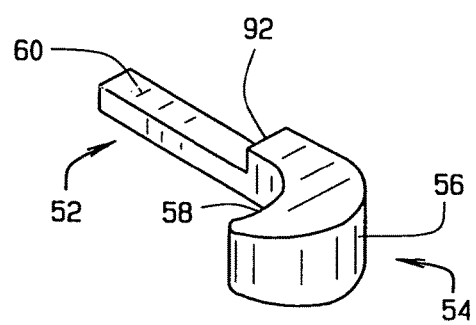
FIG. 6 is a perspective view of a lower left buccal tube constructed according to the present disclosure.

With particular reference now to FIG. 6, the upper wedge 52 is shown. The upper wedge 52 has the head portion 54 having the outer rounded contact surface 56, the inner surface 58, and the extension portion 60. The extension portion 60 is adapted for insertion into the slot opening 46 of the tube 44 for adjustment purposes. The head portion 54 also has a stop portion or surface 92 that is used for contacting the front side 80 of the tube 44. The indentations 66, which are not shown in this view, may be positioned on the extension portion 60 to capture the set screw 64 to hold the upper wedge 52 in place. In this manner, the upper wedge 52 can be repositioned in predetermined steps.

Figure 7:
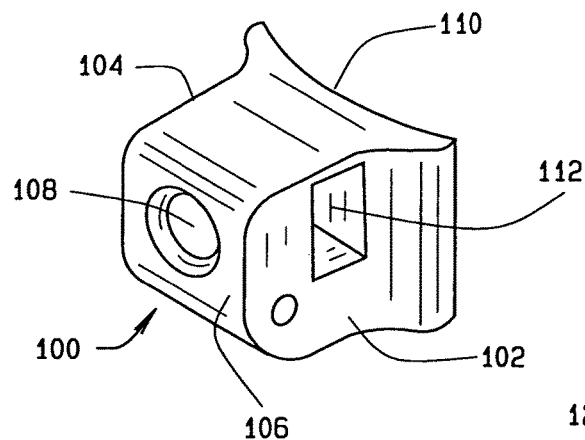
FIG. 7 is a perspective view of an upper left buccal tube constructed according to the present disclosure.

As indicated, the lower assembly 12 and the upper assembly 42 are positioned or used on the right side of a patient to assist in repositioning the mandibular jaw 38 of the mouth 40. The mandibular repositioning device 10 of the present disclosure also uses similar lower and upper assemblies on the left side of the mouth 40, and are mirror examples of each other. In particular, with reference now to FIG. 7, a perspective view of a lower left buccal tube 100 is shown. The lower left buccal tube 100 comprises a front side 102, a back side 104, a left side 106 having an opening 108 for receiving a set screw (not shown but similar to set screw 34), and a right curved attachment side 110 that is used to be welded or connected to a bracket (not shown). As has been previously indicated, the bracket is fitted on a molar. The front side 102 has an opening 112 that is offset on the side 102. Although not shown in this view, the back side 104 also has the opening.

Figure 8:
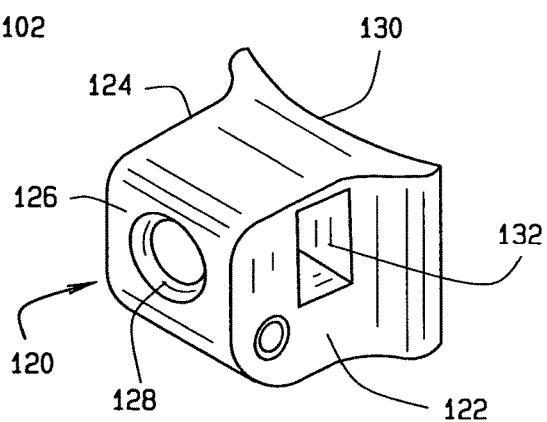
FIG. 8 is a perspective view of a lower left wedge constructed according to the present disclosure.

FIG. 8 is a perspective view of an upper left buccal tube 120. The tube 120 has a front side 122, a back side 124, a left side 126 having an opening 128 for receiving a set screw (not shown but similar to set screw 64), and a right curved attachment side 130 that is used to be welded or connected to a bracket (not shown). The front side 122 has an opening 132 that is offset on the side 122. Although not shown in this view, the back side 144 also has the same opening.

Figure 9:
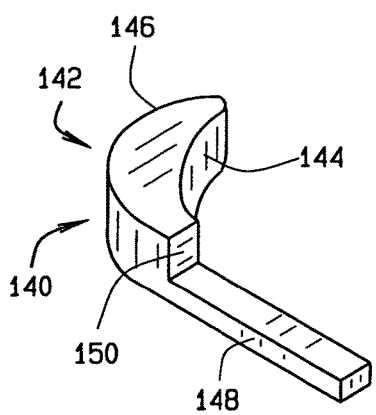
FIG. 9 is a perspective view of an upper right wedge constructed according to the present disclosure.

Referring now to FIG. 9, a perspective view of a left lower wedge 140 is shown. The left lower wedge 140 has a head portion 142 having an inner contact surface 144, an outer rounded surface 146, and an extension portion 148. The extension portion 148 is adapted for insertion into the slot opening 112 of the tube 100 for adjustment purposes. The head portion 142 also has a stop portion or surface 150 that is capable of contacting the front side 102 of the tube 100. Although not shown in this particular view, the lower wedge 140 may have indentations formed in the extension portion 148 to capture a set screw threadedly inserted into the opening 108 of the tube 100. As can be appreciated, a lower left assembly may be constructed by connecting the tube 100 to a bracket and inserting the left lower wedge 140 into the opening 132.

Figure 10:
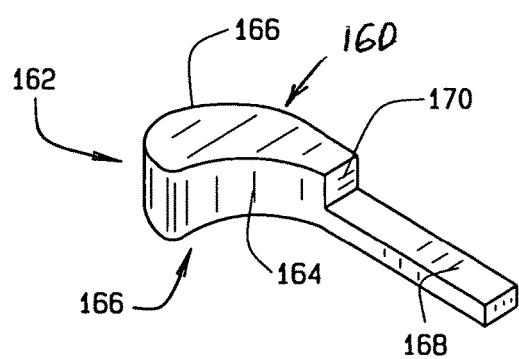
FIG. 10 is a perspective view from the opposite side of the wedge of FIG. 9.

FIG. 10 illustrates a perspective view of a right upper wedge 160. The right upper wedge 160 has a head portion 162 having an inner contact surface 164, an outer rounded surface 166, and an extension portion 168. The extension portion 168 is adapted for insertion into the slot opening 122 of the tube 120 for adjustment purposes. The head portion 162 also has a stop portion or surface 170 that is capable of contacting the front side 122 of the tube 120. Although not shown in this particular view, the upper wedge 160 may have indentations formed in the extension portion 168 to capture a set screw inserted into the opening 128 of the tube 120. A left upper assembly may be formed by welding or connecting the tube 120 to a bracket and inserting the right upper wedge 160 into the opening 132.

During treatment, the mandibular repositioning device 10 is placed over upper and lower molars on each side of the mouth 40. The wedges 22, 52, 140, and 160 may be adjusted accordingly to move the lower jaw 38 relative to the upper jaw 68. In particular, the outer rounded contact surface 56 bears against the inner contact surface 26 to put pressure on the lower jaw 38 to reposition the lower jaw 38. In this manner, the device 10 can be used to move or reposition the jaws 38 and 68 into a desired position. The indentations 36 and 66 may be used to incrementally reposition the jaws 38 and 68 over time. Over a period of treatment, the device 10 is used to move the lower jaw 38 to a correct position in the mouth 40. Once the treatment has been completed, the device 10 may be removed from the molars in the mouth 40.

Although the tubes 14, 44, 100, and 120 are described as being welded or connected to a bracket that fits over a molar, it is possible that the tubes 14, 44, 100, and 120 may be bonded directly to a molar. The various components of the right lower assembly 10, the right upper assembly 42, the left lower assembly, and the left upper assembly may be constructed of any suitable metal used for orthodontic purposes, such as 303 stainless steel.

It is also possible that the various set screws that engage through the various tubes may also threadedly engage within the various extensions to assure their engagement into their adjusted and set positions.

From all that has been said, it will be clear that there has thus been shown and described herein a mandibular repositioning device. It will become apparent to those skilled in the art, however, that many changes, modifications, variations, and other uses and applications of the subject mandibular repositioning device are possible and contemplated. All changes, modifications, variations, and other uses and applications which do not depart from the spirit and scope of the disclosure are deemed to be covered by the disclosure, which is limited only by the claims which follow.

What is claimed is:
1. A mandibular repositioning device comprising:
   a pair of lower assemblies each having a lower buccal tube having a slot opening formed therein with the tube being connected to a molar bracket that fits over a molar, a lower wedge having a head portion having an inner contact surface, an outer surface, and an integral extension portion with the extension portion being adapted for insertion into the slot opening for sliding therein for adjustment purposes, said lower buccal tubes and lower wedges being arranged outwardly of the molar to where they are applied, each tube further having a side opening through which is inserted a set screw that is adapted for contacting the extension portion for holding the lower wedge in place;

said extension portion of the lower wedge being aligned with said lower wedge, and extending rearwardly thereof and integral therewith;

and a pair of upper assemblies each having an upper buccal tube having a slot opening formed therein with the tube being connected to a molar bracket that fits over a molar, an upper wedge having a head portion having an outer rounded contact surface, an inner surface, and an integral extension portion, the extension portion being aligned with said upper wedge, extending upwardly thereof and adapted for insertion into the slot opening of a buccal tube for sliding therein for adjustment purposes, said upper buccal tubes and upper wedges also being arranged outwardly of the molar to which they are applied, the tube further having a side opening through which is inserted a set screw that is adapted for contacting the extension portion for holding the upper wedge in place with each of said outer rounded contact surfaces of said upper wedge bearing against the inner contact surface for the lower wedge of the lower assembly for repositioning a mandibular jaw;

said extension portions of the upper wedges being integrally formed therewith;

each extension portion of each lower wedge having a number of indentations or threaded openings for receiving the set screw;

each extension portion of each upper wedge having a number of indentations or threaded openings for receiving the set screw;

wherein the slot opening formed in each tube of the lower assembly is outwardly offset from the molar bracket, and where each slot opening formed in each tube of the upper assembly is outwardly offset from each tubes molar bracket;

wherein each inner contact surface of each lower wedge is a flat surface, and wherein each outer surface of each upper wedge is rounded;

wherein the rounded surface of each upper wedge is aligned with the flat surface of each lower wedge when the mandibular repositioning device is adjusted for repositioning of the lower jaw relative to the upper jaw during its application;

wherein the lower wedge of a lower assembly further includes an integral stop portion formed in its head portion for contacting the front of its associated tube; and wherein the upper wedge of one of the upper assemblies further includes an integral stop portion formed in its head portion for contacting the front of its associated tube.

* * * * *